United States Patent
Hamm et al.

(10) Patent No.: US 6,749,344 B2
(45) Date of Patent: Jun. 15, 2004

(54) CONNECTION APPARATUS FOR OPTICAL COHERENCE TOMOGRAPHY CATHETERS

(75) Inventors: Mark A. Hamm, Lynnfield, MA (US); Robert J. Crowley, Sudbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 29 days.

(21) Appl. No.: 10/039,627

(22) Filed: Oct. 24, 2001

(65) Prior Publication Data

US 2003/0077043 A1 Apr. 24, 2003

(51) Int. Cl.[7] ................................................. G02B 6/38
(52) U.S. Cl. ........................................... 385/72; 385/78
(58) Field of Search ................................ 385/72, 78, 25, 385/60

(56) References Cited

U.S. PATENT DOCUMENTS

| | | | | |
|---|---|---|---|---|
| 4,900,303 A | * | 2/1990 | Lemelson | 604/514 |
| 5,010,886 A | * | 4/1991 | Passafaro et al. | 600/439 |
| 5,026,367 A | * | 6/1991 | Leckrone et al. | 606/7 |
| 5,039,193 A | * | 8/1991 | Snow et al. | 385/25 |
| 5,371,814 A | * | 12/1994 | Ames et al. | 385/25 |
| 5,710,851 A | | 1/1998 | Walter et al. | 385/86 |
| 5,717,801 A | | 2/1998 | Smiley | 385/60 |
| 5,872,879 A | * | 2/1999 | Hamm | 385/25 |
| 6,120,516 A | | 9/2000 | Selmon et al. | |
| 6,263,133 B1 | * | 7/2001 | Hamm | 385/33 |

FOREIGN PATENT DOCUMENTS

WO    WO 97/32182 A1    9/1997

\* cited by examiner

*Primary Examiner*—Hae Moon Hyeon
(74) *Attorney, Agent, or Firm*—Orrick Herrington & Sutcliffe LLP (57) ABSTRACT

An optical catheter connection system is described which has two mating assemblies: a motor unit and an optical catheter connector. The optical catheter connector mates to the motor unit for coupling optical signal into and out of a catheter optical fiber and providing drive torque to the catheter optical fiber. The motor unit includes a rotary shaft powered by a motor for providing drive torque to the catheter optical fiber to rotate the fiber. The motor unit further includes a split sleeve for aligning a motor optical fiber with the catheter optical fiber for coupling optical signals between the two fibers. In one embodiment, a shield is provided around the outer surface of the optical catheter connector to help maintain a sterile field by forming a barrier between a clinician's sterile hand, which holds the optical catheter connector, and the non-sterile motor unit.

6 Claims, 9 Drawing Sheets

CONNECTION APPARATUS FOR OPTICAL COHERENCE TOMOGRAPHY CATHETERS

BACKGROUND OF THE INVENTION

1. Field of the Invention

The present invention relates to medical device connectors, and more particularly to optical catheter connectors.

2. Background

Optical Coherence Tomography (OCT) is an optical imaging technique, which achieves non-invasive, cross-sectional imaging of a patient's body. OCT is analogous to ultrasound imaging, only measuring the intensity of back-scattered infrared light rather than ultrasound. To image the blood vessel of a patient using OCT, an optical catheter is inserted into the blood vessel. An optical signal is transmitted through an optical fiber in the optical catheter and emitted at the distal end of the catheter into the blood vessel. The optical signal is typically produced by a laser, e.g., laser diode. The optical signal reflected back to the catheter from the blood vessel and surrounding tissue is transmitted through the optical fiber to an interferometer, which optically processes the reflected optical signal to obtain a depth image of the blood vessel.

An OCT connection system couples optical signals produced by a light source, e.g, laser, into the catheter optical fiber to be emitted inside the body. The OCT connection system then couples the reflected optical signal out of the catheter optical fiber to an interferometer to obtain a image of the inside of the body. In addition, the OCT connection system may include a motor unit for providing drive torque to the catheter optical fiber to rotate the catheter optical fiber during imaging. This enables a radial cross-sectional image of the inside of the body to be obtained.

There are many challenges in designing a high performance, ergonomic catheter connector. The requirements of a good connector design include sterile field maintenance, reliable high performance components, ease of assembly and an intuitive connection procedure. A good design should provide a connection system that meets all these requirements while keeping the cost of the disposable portion of the connector low. The design should provide a positive lock between a catheter connector and a motor unit to prevent accidental disconnection of the catheter or degradation of performance if the catheter is used to pull the motor unit. It should also provide a clear indication that proper engagement between the catheter connector and the motor unit is achieved.

SUMMARY OF THE INVENTION

The invention provides an OCT connection system comprising two mating assemblies, a motor unit and an OCT catheter connector. The OCT catheter connector mates to the motor unit for coupling optical signals into and out of a catheter optical fiber and for providing drive torque to the catheter optical fiber.

A motor unit, built in accordance with a first example embodiment of the invention, includes a motor nose with an opening at its distal end, a rotary shaft housed in the motor nose, a connector assembly housed in and attached to the rotary shaft, and a fiber-to-fiber adapter mounted to the rotary shaft. The rotary shaft, the connector assembly and the fiber-to-fiber adapter all rotate together within the motor nose and form the mechanical rotating portion of the motor unit. The motor unit further includes a motor optical fiber that runs along the rotational axis of the connector assembly. One end of the motor fiber is supported by a motor fiber ferrule, which is inserted into one end of a split sleeve in the fiber-to-fiber adapter. As used here, the term "ferrule" refers to a hollow structure of any shape or configuration. For example, while preferably the motor fiber ferrule is cylindrical, it can be hexagonal. As another example, a motor fiber ferrule may be a hollow band surrounding the motor optical fiber and protects or gives support to the motor optical fiber.

The OCT catheter connector includes a catheter ferrule with an opening at its proximal end, a connector bushing rotatably housed within the catheter ferrule, and an optical fiber catheter connector attached to the connector bushing. The OCT connector also includes a catheter optical fiber that runs along the rotational axis of the catheter fiber connector. One end of the catheter optical fiber is supported by a catheter fiber within the catheter fiber connector.

The OCT catheter connector is mated to the motor unit by inserting the fiber connector into the fiber-to-fiber adapter through the opening in the motor nose. As the fiber connector is inserted into the fiber-to-fiber connector, the catheter fiber ferrule supporting the catheter optical fiber is inserted into the other end of the split sleeve in the fiber-to-fiber adapter. The split sleeve aligns the catheter optical fiber with the motor optical fiber to couple optical signals between the two fibers. The fiber-to-fiber adapter includes retaining clips for locking the catheter fiber connector in place once proper engagement is achieved. The opening of the motor nose is equipped with tab slots adapted to receive snap lock tabs on the OCT catheter connector. Once the OCT catheter connector is properly mated to the motor unit, the rotary shaft provides drive torque to the catheter fiber connector and the catheter optical fiber via the fiber-to-fiber adapter.

The snap locks of the OCT catheter connector may include grippers for pushing the catheter fiber connector into proper engagement with the fiber-to-fiber adapter. To do this, the grippers engage slots on the connector bushing through slot openings in the catheter ferrule. This engagement holds the connector bushing stationary with respect to the catheter ferrule so that the connector bushing pushes the catheter fiber connector into the fiber-to-fiber adapter as the OCT catheter connector is inserted into the motor unit. When proper engagement is achieved, the grippers retract from the slots on the connector bushing, allowing the catheter fiber connector to freely rotate within the catheter ferrule of the OCT catheter connector.

The OCT catheter connector may include an 'O'-ring fitted around a grooved portion of the catheter fiber connector to provide a dynamic seal to block fluid from contaminating the catheter fiber connector. The OCT catheter also may include a free floating 'O'-ring housing to compensate for any eccentric rotation of the catheter fiber connector.

An OCT catheter connector, built in accordance with a second example embodiment, comprises a flexible catheter ferrule and a rigid retainer within the catheter ferrule. The retainer provides rigidity to the catheter ferrule. The OCT catheter connector also includes a connector bushing and a catheter fiber connector attached to the connector bushing. The connector bushing may include ribs that are positioned at cutouts in the retainer.

The OCT catheter connector according to this second example embodiment is mated to the motor unit by slightly squeezing a grip area of the catheter ferrule corresponding to the cutouts of the retainer. The squeezing deforms the catheter ferrule within the grip area, causing the catheter ferrule to contact the ribs of the connector bushing through the cutouts in the retainer. This contact holds the connector bushing stationary with respect to the OCT catheter connector so that the connector bushing pushes the catheter fiber connector into engagement with the motor unit as the OCT catheter connector is inserted into the motor unit. Once the OCT catheter connector is properly mated to the motor unit, the catheter ferrule elastically regains its original shape, allowing the connector bushing and the catheter fiber to freely rotate within the catheter ferrule.

The OCT connector according to this second example embodiment also preferably includes a shield running around the outer cylindrical surface of the catheter ferrule to help maintain a sterile field by forming a barrier between a clinician's sterile hand, which holds the OCT connector, and the non-sterile motor unit. The OCT connector also may have short ribs on the outer cylindrical surface of the catheter ferrule to snap into mating grooves in the motor unit to prevent unwanted disconnection of the OCT connector from the motor unit.

A motor unit, built in accordance with a third example embodiment, includes three spring loaded ball plungers radially located preferably 120 degrees apart on the motor nose. Each one of the three ball plungers has a spherical ball positioned to engage a corresponding concave depression in the OCT catheter connector to secure the OCT connector to the motor unit via frictional resistance. The motor nose further may include a bendable wave or Belleville washer surrounding the fiber-to fiber adapter of the motor unit.

To insert the OCT connector into the motor unit, the catheter ferrule of the OCT connector is pushed into the motor unit. As the catheter ferule is pushed into the motor unit, the distal end of the connector bushing contacts a portion of the inner wall of the catheter ferrule. This contact causes the portion of the inner wall of the catheter ferrule to push against the connector bushing, which in turn causes the connector bushing to push the catheter fiber connector into engagement with the fiber-to-fiber adapter of the motor unit. Also during insertion of the OCT connector into the motor unit, the proximal end of the catheter ferrule pushes the washer surrounding the fiber-to-fiber adapter inwardly. When the catheter ferrule is released after proper engagement has been achieved, the washer pushes the catheter ferrule distally with respect to the connector bushing. This causes the portion of the inner wall of the catheter ferrule to move away from the connector bushing, allowing the connector bushing to rotate freely within the catheter ferrule without friction or side loading.

The catheter ferrule according to this third example embodiment may be constructed of a rigid, injection moldable material as one piece or two pieces comprising a shield that is bonded to the cylindrical body of the ferrule that acts as a sterile barrier to prevent the contamination of the clinician's sterile hand during attachment of the catheter to the non-sterile motor unit.

The OCT connector according to this third example embodiment may include drain holes to allow fluid leakage to drain through the wall of the ferrule to reduce the likelihood of contamination of the motor unit and the fiber optic connector if the 'O'-ring seal should leak during high-pressure infusion. In addition, the 'O'-ring according to this embodiment seals around a gland instead of a grooved portion of the catheter connector. The gland is a stainless steel tube with a smooth outer surface finish that is bonded into the catheter fiber connector using epoxy to form a high pressure seal.

The details presented in this Section are provided as illustrative examples only, are not necessarily required by the invention and should not be used to limit the scope of the invention. Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
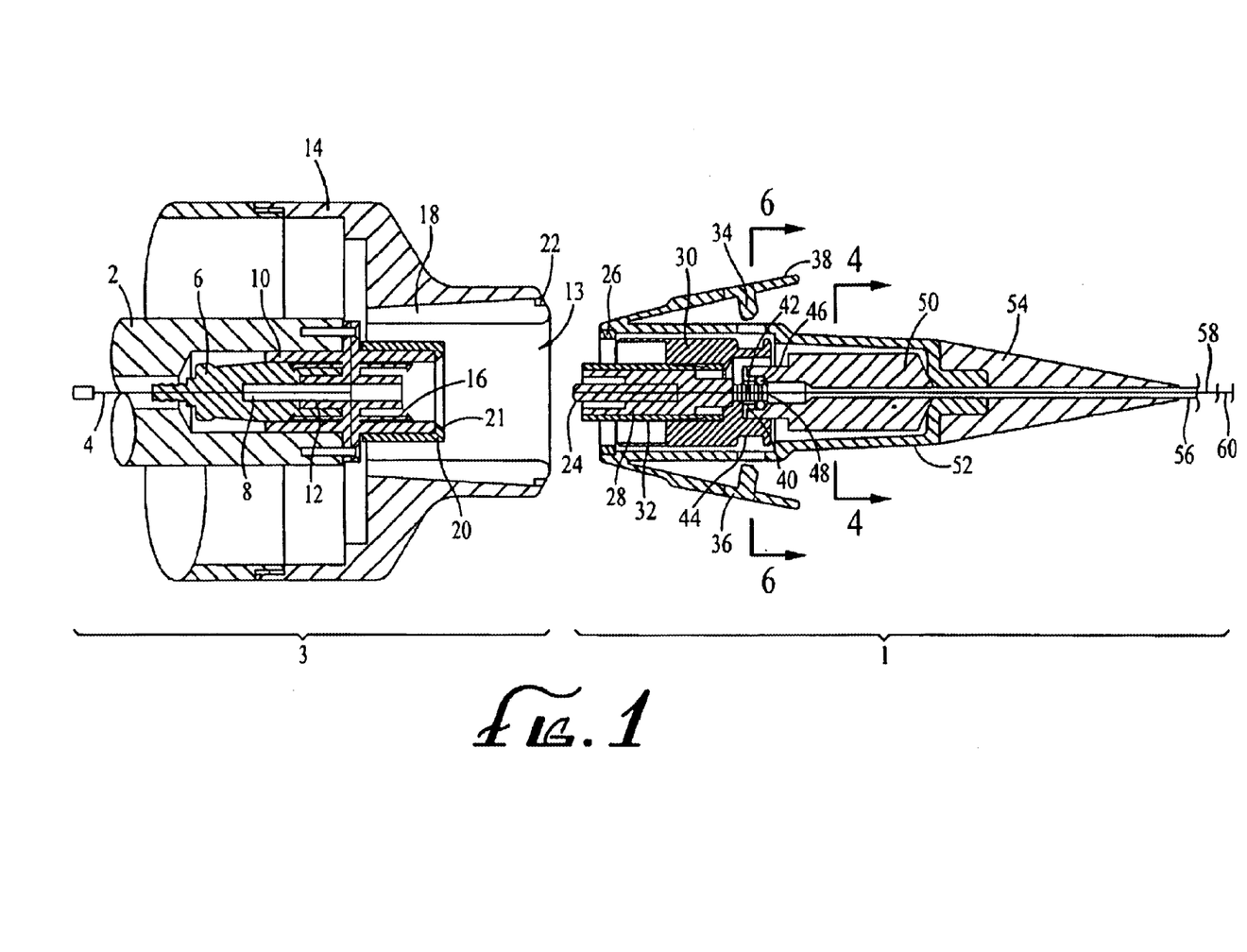
FIG. 1 shows an axial cross-sectional view of a first embodiment of an improved OCT catheter connection system.

FIG. 1 illustrates an axial cross-sectional view of a first example embodiment of an OCT catheter connection system. The OCT catheter connection system comprises two mating assemblies, an OCT catheter connector 1 and a motor and optical rotary joint unit 3, hereinafter, the "motor unit" for simplicity. The distal portion of the motor unit 3 is shown in FIG. 1.

The motor unit 3 includes a motor nose 14 with an opening 13 at its distal end, a rotary shaft 2 housed in the motor nose 14, a connector assembly 6 housed in and attached to the rotary shaft 2, and a fiber-to-fiber adapter 10 mounted to the rotary shaft 2 with screws. The rotary shaft 2, the connector assembly 6 and the fiber-to-fiber adapter 10 all rotate together within the motor nose 14 and form the mechanical rotating portion of the motor unit 3. The motor unit 3 also includes a motor optical fiber 4 that runs along the rotational axis of the connector assembly 6. The motor optical fiber 4 may be a single-mode or a multiple-mode optical fiber. The fiber-to-fiber adapter 10 includes a split sleeve 12, which may be made of ceramic or metal. One end of the motor optical fiber 4 is supported by a motor fiber ferrule 8, which is inserted into one end of the split sleeve 12.

Figure 2:
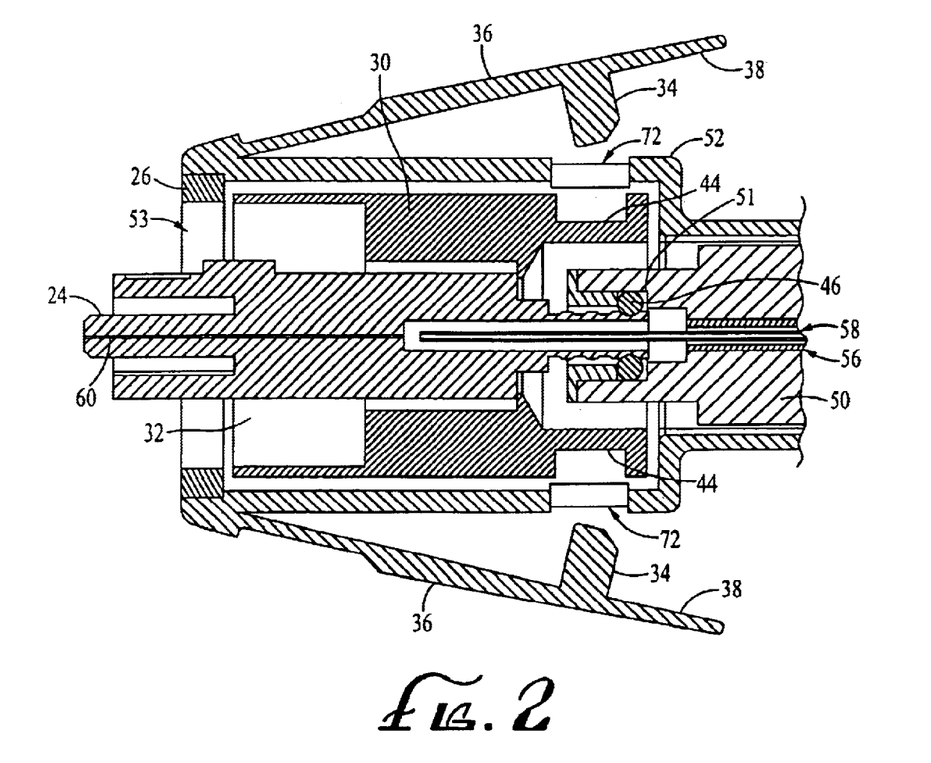
FIG. 2 shows a blown-up axial cross-sectional view of the OCT catheter connector.
Figure 3:
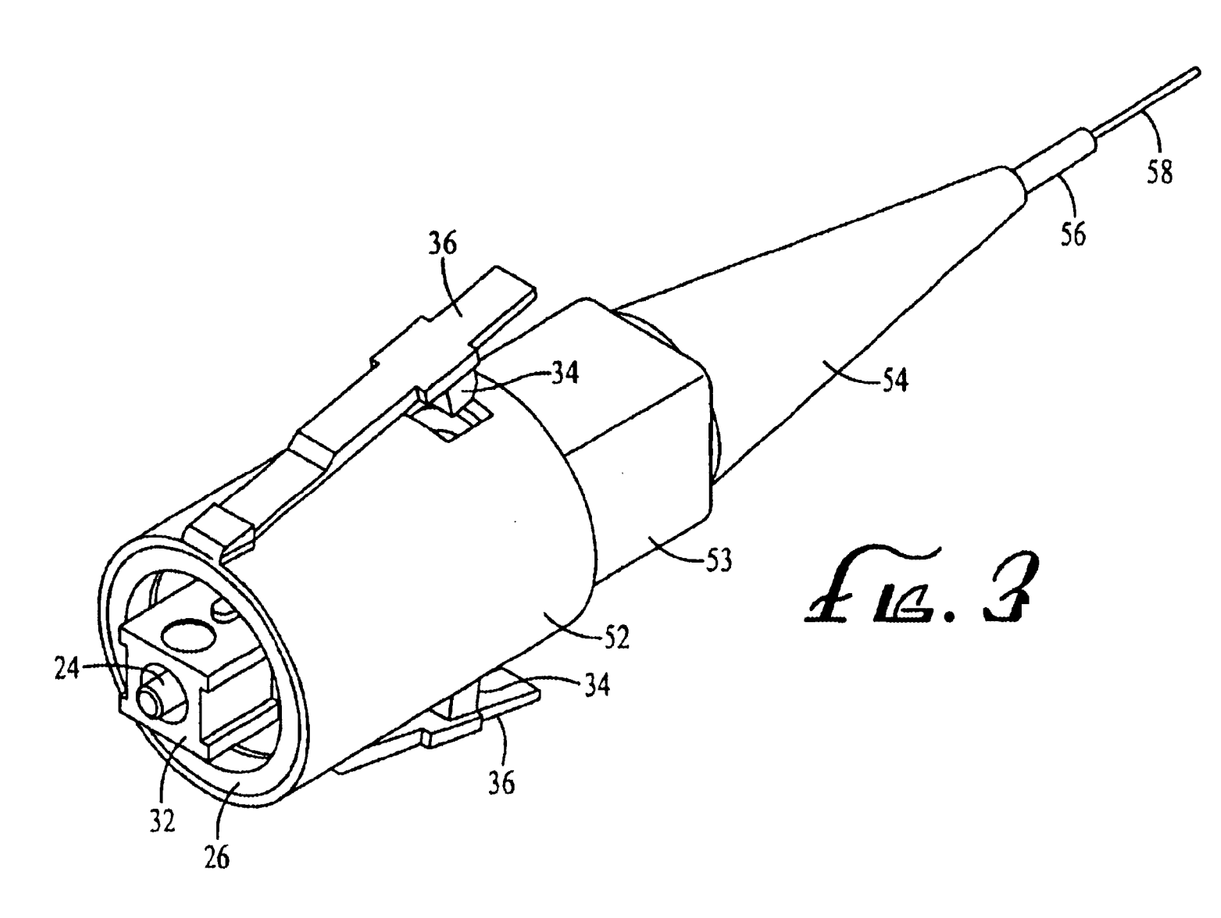
FIG. 3 shows a perspective view of the OCT catheter connector.

FIG. 2 shows a blown up cross-sectional view and FIG. 3 shows a perspective view of the OCT catheter connector 1.

The OCT catheter connector 1 includes a hollow catheter ferrule 52 with an opening 53 at its proximal end and a connector bushing 30 housed in the catheter ferrule 52. The catheter ferrule 52 is preferably made of polycarbonate or injection-molded plastic. Space is provided between the connector bushing 30 and the inner walls of the catheter ferrule 52 so that the connector bushing 30 can freely rotate within the catheter ferrule 52. A retainer 26 is provided along the opening 53 of the catheter ferrule 52 to prevent the connector bushing 30 from falling out of the catheter ferrule 52. The OCT catheter connector 1 further includes a fiber connector 32 attached to the connector bushing 30, e.g., with epoxy, and a catheter optical fiber 60 that runs along the rotational axis of the catheter fiber connector 32. One end of the catheter fiber 60 is supported by a catheter fiber ferrule 24 attached to the catheter fiber connector 32. The catheter fiber ferrule 24 extends outwardly from the opening 53 of the catheter ferrule 52. The OCT catheter connector 1 also preferably includes snap lock tabs 36 attached to the outer surface of the catheter ferrule 52. Preferably, the snap lock tabs 36 are made of a semi-rigid material, such as plastic, so that they can be compressed, e.g., by a clinician's fingers. The snap lock tabs 36 may be made of the same piece as the catheter ferrule 52 or may be made of separate pieces attached to the catheter ferrule 52, e.g., with epoxy.

Figure 5:
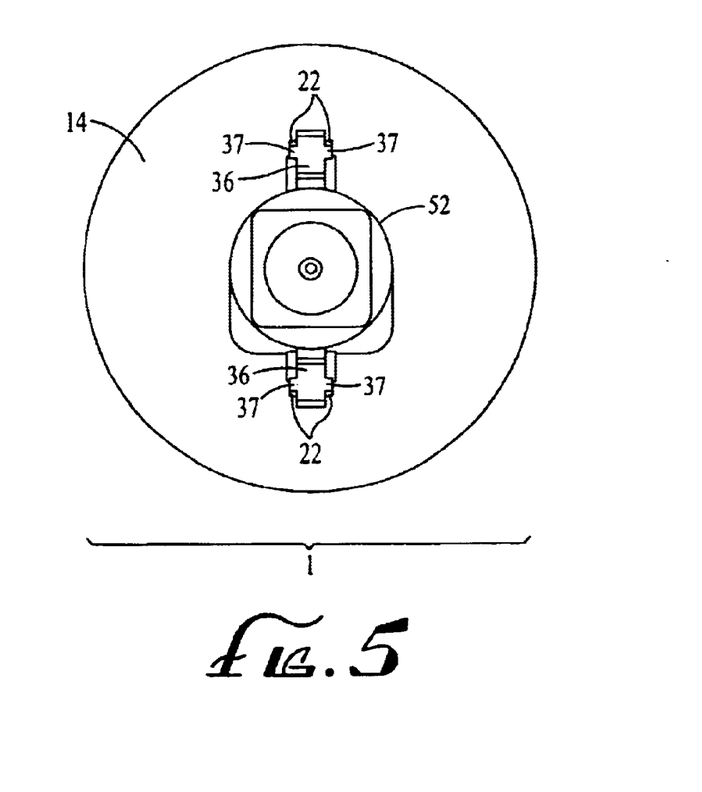
FIG. 5 shows an end view of the OCT catheter connector and the motor unit looking proximally.

Referring to FIG. 1, the OCT catheter connector 1 is mated to the motor unit 3 by inserting the catheter fiber connector 32 into the fiber-to-fiber adapter 10 through the opening 13 in the motor nose 14. As the fiber connector 32 is inserted into the fiber-to-fiber adapter 10, the catheter fiber ferrule 24 is inserted into the other end of the split sleeve 12. The split sleeve 12 aligns the catheter optical fiber 60 with the motor optical fiber 4 to couple optical signals between the two fibers 60 and 4. A guide 20 bonded to the fiber-to-fiber adapter 10, e.g., with epoxy, provides guidance for the catheter fiber connector 32 into the fiber-to-fiber adapter 10 in case of slight misalignment during insertion. The fiber-to-fiber adapter 10 includes retaining clips 16 for locking the catheter fiber connector 32 in place once proper engagement is achieved. The retaining clips 16 prevent the catheter fiber connector 32 from being detached from the motor unit 3 by pulling the catheter shaft 56 (discussed later) of the OCT connector 1. The opening 13 of the motor nose 14 has tab slots 18 adapted to receive the snap lock tabs 36 of the OCT catheter connector 1. The snap lock tabs 36 are locked in the tab slots 18 by protuberances 22 on the tab slots 18. The protuberances 22 are best illustrated in FIG. 5, which shows a front view of the OCT connector 1 mated to the motor unit 3. Each snap lock tab 36 includes flanges 37 adapted to engage the protuberances 22. The snap lock tabs 36 are compressed as the OCT connector 1 is inserted into the motor unit 3, allowing the flanges 37 to clear the protuberances 22 on the tab slots 18. Once the snap lock tabs 36 are inserted into the tab slots 18 and released, the flanges 37 engage the protuberances 22, thereby locking the snap lock tabs 36 in the tab slots 18. Preferably, an audible click is produced when the snap lock tabs 36 snap into place in the tab slots 18. Once the OCT catheter connector 1 is mated to the motor unit 3, rotation of the rotary shaft 2 by a motor (not shown) provides drive torque to the catheter fiber connector 32 and the catheter fiber 60 via the fiber-to-fiber adapter 10.

The catheter fiber connector 32 is detached from the motor unit 3 by compressing finger tabs 38 on the snap lock tabs 36. This allows the flanges 37 on the snap lock taps 36 to clear the protuberances 22 on the tab slots 18 and the OCT connector 1 to be pulled out of the motor unit 3.

The snap lock tabs 36 includes grippers 34 for providing insertion force to the catheter fiber connector 32 to push the catheter fiber connector 32 into proper engagement with the fiber-to-fiber adapter 10. To do this, the snap lock tabs 36 are compressed so that the grippers 34 engage slots 44 on the connector bushing 30 through slot openings 72 in the catheter ferrule 52. The grippers 34 hold the connector bushing 30 stationary with respect to the OCT connector 1 so that the bushing 30 pushes the catheter fiber connector 32 into the fiber-to-fiber adapter 10 as the OCT connector 1 is inserted into the motor unit 3. The grippers 34 retract when the snap lock tabs 36 click into place in the tab slots 18 when, and thereby indicating, proper engagement has been achieved. This allows the connector bushing 30 and the catheter connector 32 to freely rotate within the catheter ferrule 52 without any support other than that provided by the fiber-to-fiber adapter 10 of the motor unit 3. This is important because any lateral forces acting on the catheter fiber connector 32 during rotation can cause flexing of the 'optical connection', which can result in unwanted losses or variation in optical power coupled into the catheter fiber 60.

A seal 46, preferably, an 'O'-ring, is optionally used to provide a dynamic seal to block fluid from contaminating the OCT catheter connector 1. The 'O'-ring 46 is fitted around a grooved portion of the catheter fiber connector 32. The 'O'-ring 46 also provides frictional resistance to rotation of the catheter fiber connector 32 so that it retains its rotational position relative to the catheter ferrule 52 when the OCT catheter connector 1 is detached from the motor unit 3. A relatively large clearance is provided between the connector bushing 30 and the inner wall of the catheter ferrule 52 to allow the bushing 30 to freely rotate, even when the bushing 30 rotates eccentrically.

Figure 4:
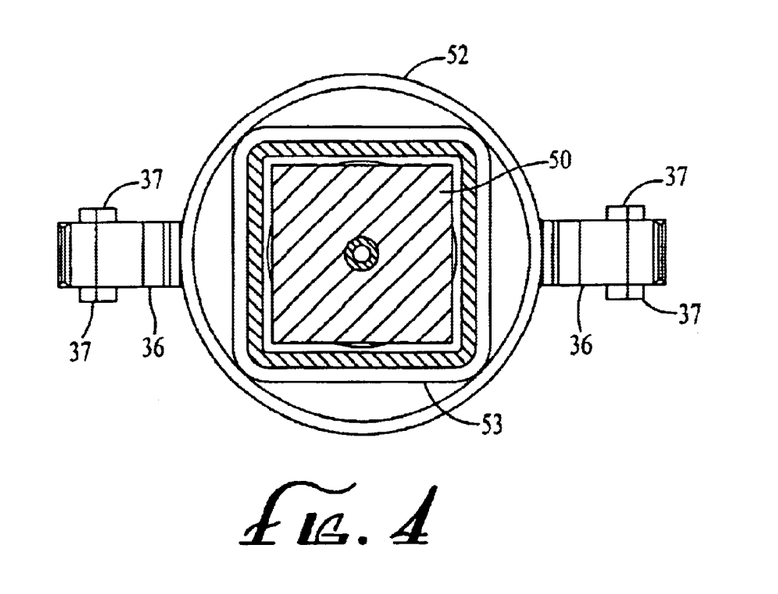
FIG. 4 shows a radial cross-sectional view of the OCT catheter connector taken along line 4—4.

The OCT catheter connector 1 further includes an 'O'-ring housing 50 within the catheter ferrule 52. The 'O'-ring housing 50 has an annular slot that fits around the 'O'-ring 46. The catheter fiber 60 runs through the axis of the 'O'-ring housing 50. The 'O'-ring housing 50 is free floating within the catheter ferrule 52 without any rigid mounts in order to compensate for any eccentric rotation of the catheter fiber connection 32. A relatively large clearance is provided between the 'O'-ring housing 50 and the catheter ferrule 52 to allow the 'O'-ring housing 50 to follow an orbit as the catheter fiber connector 32 rotates in an eccentric path. In this example embodiment, the 'O'-ring housing 50 has a square outer profile and the portion 53 of the catheter ferrule 52 enclosing the 'O'-ring housing 50 has a corresponding a square inner profile. This is best illustrated by FIG. 4, which shows a cross sectional view of the portion 53 of the catheter ferrule 52 enclosing the 'O'-ring housing 50. The square inner profile 53 of catheter ferrule 52 prevents the 'O'-ring housing 50 from rotating inside the catheter ferrule 52. This is done to provide resistance to rotational forces on the 'O'-ring housing as the grooved portion of the catheter fiber connector 32 rotates inside the 'O'ring 46. Clearance is provided between the 'O'-ring housing 50 and the inner wall of the catheter ferrule 52 to allow the 'O'-ring housing 50 to float inside the catheter ferrule 52.

A flexible drive shaft 58 is provided for rotating the catheter fiber 60 inside a human body. The drive shaft 58 encloses the catheter fiber along the length of the catheter outside of the fiber connector. The drive shaft 58, preferably, possesses both a high torsional stiffness and a low bending stiffness. This allows the drive shaft 58 to rotationally drive the catheter fiber 60 while allowing the drive shaft 58 to bend along the path of a body lumen. The drive shaft 58 may, for example, be made of two counterwound layers of multifilar coils, which are commonly used in intravascular Ultrasound (IVUS) catheters. The proximal end of the driveshaft 58 is sealed onto the catheter connector 32, e.g., with epoxy 48, to create a liquid tight seal to prevent fluid from contaminating the catheter fiber connector 32. A conical strain relief 54 is proved at the tip of the OCT catheter connector 1 to prevent damage to the catheter fiber 60 or the drive shaft 58 by evenly distributing bending forces as the catheter is pulled to the side. The OCT connector further includes a catheter shaft 56 running through the axis of the 'O'-ring housing 50 and the conical strain relief 54. The catheter shaft 56 is attached to the 'O'-ring housing, e.g., with epoxy. Of course, any structures in any embodiment which are attached by epoxy or adhesive can instead be attached by any other means. The drive shaft 58 runs through the catheter shaft 56 and rotates inside the catheter shaft 56.

FIG. 5 shows a front-end view of the OCT catheter connector 1 and the motor unit 3. This view shows that the shape of the catheter ferrule 52 is preferably asymmetrical so that there is only a one-way fit of the catheter connector 1 into the motor nose 14. This is desirable because the ends of the optical fibers 4 and 60 are preferably angled to minimize back reflection of the optical signal. Because the ends of optical fibers 4 and 60 are angled, they have to be coupled together at a particular orientation. The one-way fit of the catheter connector 1 into the motor nose is used to ensure that the catheter fiber 60 is properly orientated with the motor fiber 4. This prevents an operator from trying to force the catheter fiber connector 32 into the fiber-to-fiber adapter 10 in an improper orientation, which could cause damage to one or both ends of the optical fibers 4 and 60.

Figure 6:
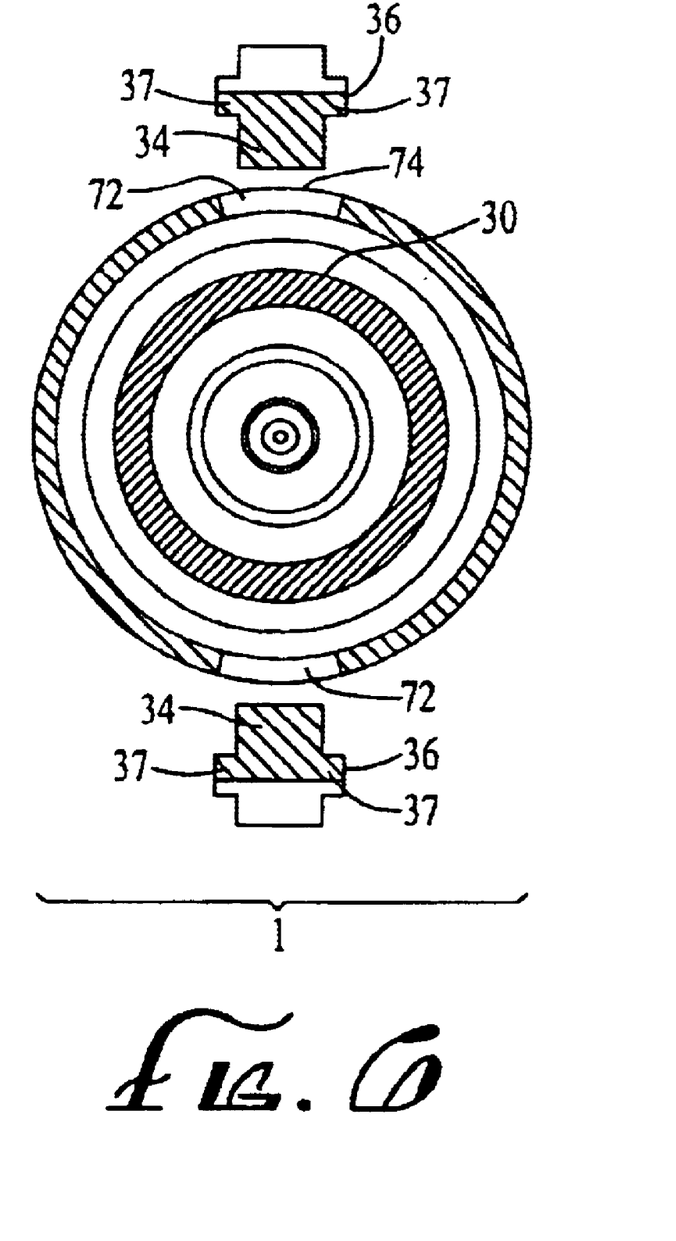
FIG. 6 shows a radial cross-sectional view of the OCT catheter connector taken along line 6—6.

FIG. 6 shows a radial cross-sectional view of the OCT connector 1 taken through the grippers 34 and looking distally. The catheter ferrule wall 74 has two slots 72 through which the grippers 34 contact the adapter 30 to push the catheter fiber connector 32 into proper engagement with the fiber-to-fiber adapter 10.

Figure 7:
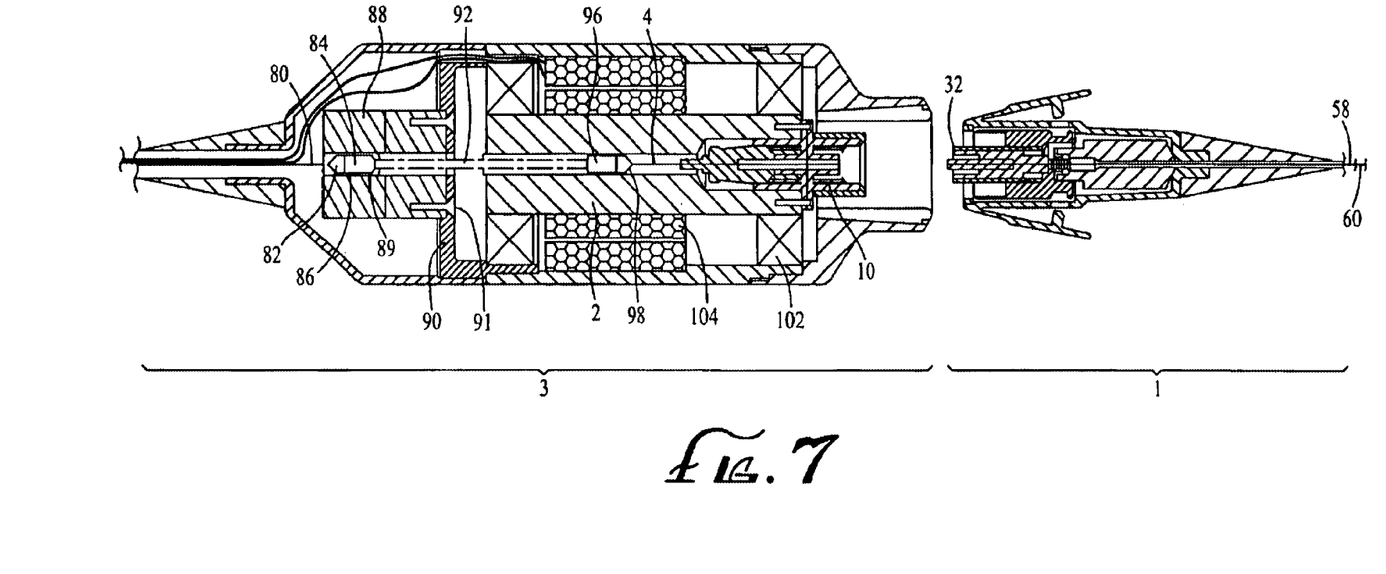
FIG. 7 shows an axial cross-sectional view of the motor unit of the OCT catheter connection system.

FIG. 7 shows an axial cross-sectional view of the OCT connection system, in which the entire motor unit 3 is shown. Light from a light source (not shown), e.g., a laser, enters the OCT connection system through an optical fiber 80, which is part of a connector/fiber/lens assembly 82. The light in the fiber 80 is collimated by a GRIN lens 84. The lens housing 86 is mounted to a five-axis positioner 88 with epoxy 89. The five-axis positioner 88 is mounted to positioner mount 90 with screws and is rotationally stationary. The five-axis positioner 88 allows adjustment of the collimated beam 92 from the lens 84 such that its optical axis is collinear with the rotational axis of the shaft rotary shaft 94. The collimated beam 92 enters a GRIN lens 96 of the lens/fiber/connector assembly 98, which can rotate within the motor unit 3. The lens/fiber/connector assembly 98 is adjusted with an active feedback system such that its optical axis is collinear and concentric with the rotational axis of the rotary shaft 94. The GRIN lens 96 focuses the collimated beam 92 into the motor fiber 4, which transmits an optical signal from the catheter optical fiber 60 when the two fibers 4 and 60 are coupled together. The motor unit 3 also transmits the reflected beam received from the catheter optical fiber 60 along the same optical path to the optical fiber 80. The optical fiber 80 then transmits the reflect beam to an interferometer (not shown) to be processed.

The rotary shaft 2 rotates with two precision bearings 102 and is rotated by a motor 104, which provides drive torque to rotate the shaft 2 and the fiber-to-fiber adapter 10. When the motor unit 3 and the OCT catheter connector assembly 1 are mated, the fiber-to-fiber adapter 10 transfers this drive torque to rotate the catheter fiber connector 32, the catheter fiber 60 and the flexible drive shaft 56 of the catheter connector 1.

Figure 8:
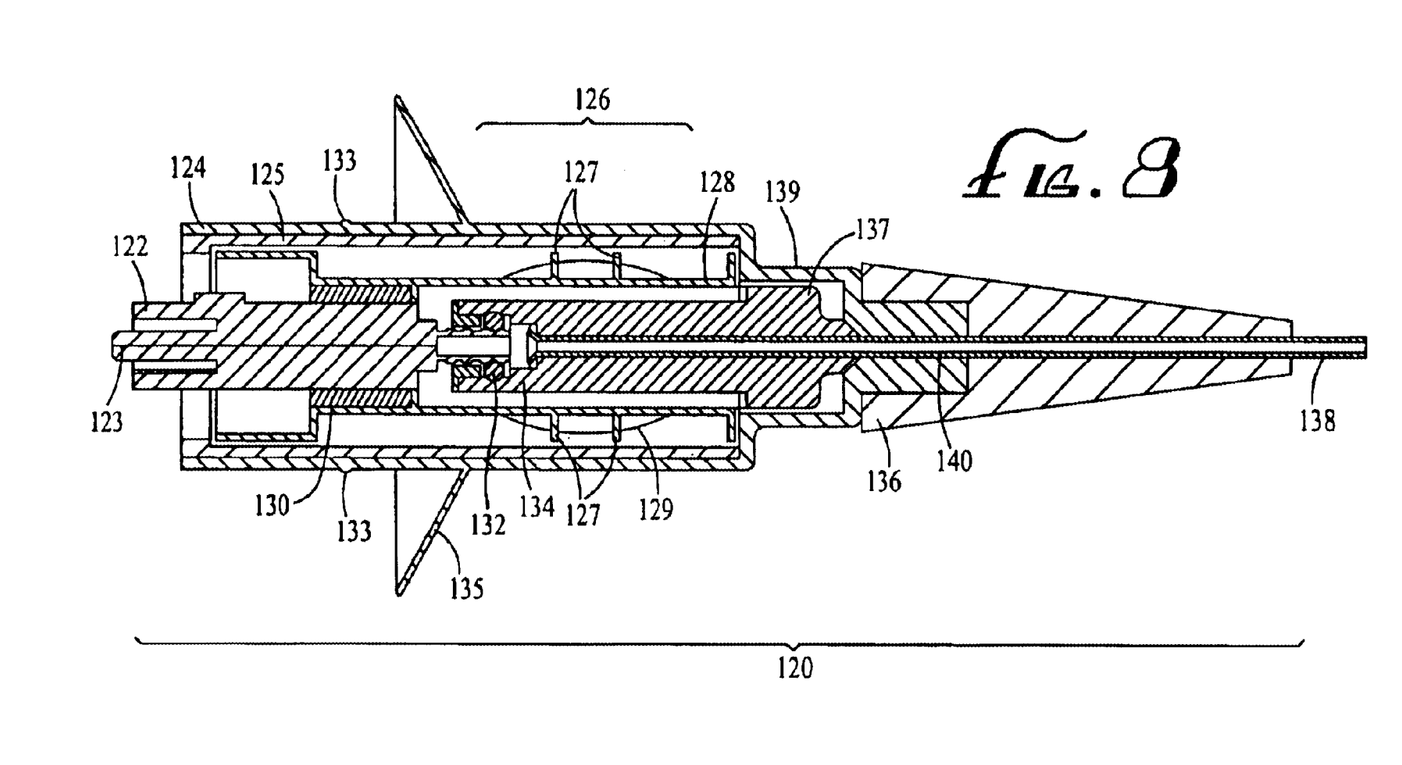
FIG. 8 shows an axial cross-sectional view of a second embodiment of an improved OCT catheter connector.

FIG. 8 shows an axial cross-section of an OCT catheter proximal connector 120 according to a second example embodiment. The OCT catheter connector 120 includes a catheter ferrule 124 and a retainer 125 within the catheter ferrule 124. The catheter ferrule 124 is constructed of a soft flexible polymer, such as PEBAX 2533. The retainer 125 is constructed of a rigid polymer such as polycarbonate or PEEK to provide rigidity to the catheter ferrule 124. The OCT catheter connector 120 further includes a connector bushing 128 rotatably housed in the retainer 125 and a catheter fiber connector 122 attached to the connector bushing 128 by an epoxy 130. The connector bushing 128 has ribs 127 positioned at elliptical cutouts 129 in the retainer 125. The catheter optical fiber 123 runs along the rotational axis of the catheter fiber connector 122.

The OCT catheter connector 120 according to this embodiment is mated to a motor unit (not shown) by slightly squeezing a grip area 126 of the catheter ferrule 124 corresponding to the elliptical cutouts 129 of the retainer 125. This deforms the cylindrical cross-section of the catheter ferrule 124 within the grip area 126, causing the ferrule 124 to contact ribs 127 of the connector bushing 128 through the cutout 129 of the retainer 125. This mechanism provides a means for grasping and/or transferring force to the catheter fiber connector 122 to push it into proper engagement with the motor unit (not shown). When the OCT catheter connector 120 is mated to the motor unit, the catheter ferrule 124 elastically regains its original shape, allowing the connector bushing 128 and the catheter fiber connector 122 to freely rotate with no friction or side loading forces that negatively affects the sensitive fiber connection. The retainer 125 extends the entire length of the cylinder portion of the ferrule 124, providing rigidity to transfer loads from the catheter without interfering with the free rotation of the catheter fiber connector 122 and the connector bushing 128. As in the previous embodiment, a seal 132, preferably an 'O'-ring, is provided to prevent fluids from contaminating the catheter fiber connector 122 and the motor unit. Preferably, the 'O'-ring housing 134 is substantially cylindrical, except for a square portion 137 housed in a square portion 138 of the catheter ferrule 124 to resist rotational forces caused by friction between the catheter fiber connector 122 and the 'O'-ring 132 during rotation. The catheter ferrule 124 can also be used to prevent rotation of the catheter caused by friction imparted to the seal 132 by bonding the catheter shaft 138 inside the strain relief 136 or the catheter ferule 124 with epoxy 140. The catheter ferrule 124 is held rotationally stationary through frictional contact with the motor nose, which is not shown in this detail, but is substantially equivalent to those described in the previous embodiments.

The OCT connector 120 according to this embodiment also includes a shield 135 running around the outer cylindrical surface of the catheter ferrule 124 to help maintain a sterile field by forming a sterile barrier between the clinician's sterile hand, which holds the OCT catheter connector 120 during the connection procedure, and the non-sterile motor unit (not shown). Other imaging catheter connection procedures require the non-sterile motor unit to be bagged in a polyethylene bag to reduce the risk of sterile field contamination. While the polyethylene bag provides a sterile barrier between the clinician's hand and the motor unit, it sometimes prevents proper engagement between the catheter connector and the motor unit because it must extend over the distal end of the motor unit to serve as an effective shield. The shield 135 also serves as a means to prevent the clinician's hand from slipping as he or she pushes the OCT connector into engagement with the motor unit. The catheter ferrule has short ribs 133 on its outer cylindrical surface, which mates with a cylindrical depression on the motor unit. The short ribs 133 snap into mating grooves in the cylindrical depression of the motor unit. This engagement provides a positive locking mechanism to prevent unwanted disconnection of the OCT catheter connector 120 in case of strong tensile force applied to the catheter shaft 138.

Figure 9:
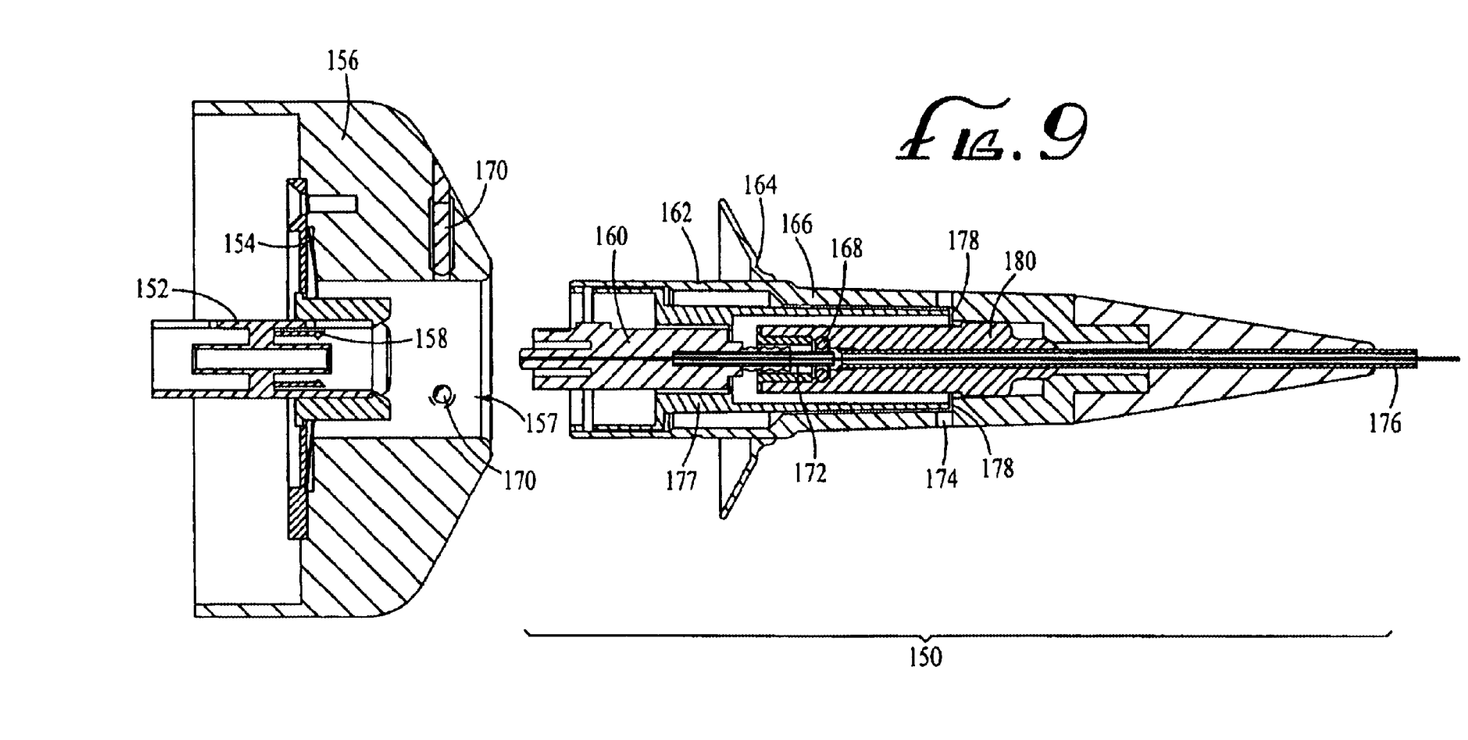
FIG. 9 shows an axial cross-sectional view of a third embodiment of an improved OCT connection system.

FIG. 9 shows an axial cross-section of a third example embodiment of the OCT catheter connector 150. This embodiment preferably performs all the functions described in the previous embodiments, but utilizes components that are less expensive to fabricate and reduces the component count as well. Some of the desirable features of a good connection system include a quick and easy attachment procedure using one sterile hand, clearly identifiable alignment indicators and a positive indication of proper engagement, e.g., an audible click. This embodiment avoids the use of a plastic bag that serves as a sterile barrier for the motor unit in IVUS products and the embodiment shown in FIG. 1 interfering with the finger tabs function.

The motor unit according to this example embodiment includes three spring-loaded ball plungers 170 radially located 120 degrees apart on the opening 157 of the motor nose 156. Each of the three ball plungers 170 has a spring loaded spherical ball adapted to engage a corresponding concave depression 162 in the catheter ferrule 166. This engagement secures the OCT connector 150 to the motor unit via frictional resistance, which resists torsional forces from the seal 168, such as an 'O'-ring, and pulling forces from the catheter. The motor nose 156 includes a bendable wave or Belleville washer 154 secured to the inside the motor nose 156 and surrounding the fiber-to-fiber adapter 152.

To insert the OCT connector 150 into the motor unit, a clinician grips the catheter ferrule 166 and pushes it into the motor unit. As the catheter ferrule 166 is pushed into the motor unit, the distal end of the connector bushing 177 contacts a portion 178 of the inner wall of the catheter ferrule 166. This contact causes the portion 178 of the inner wall to push against the connector bushing 177, which in turn causes the connector bushing 177 to push the catheter fiber connector 160 into engagement with the fiber-to-fiber adapter 152. Also during insertion of the OCT connector 150 into the motor unit, the proximal end of the catheter ferrule 166 pushes the washer 154 inwardly. When the clinician releases the catheter ferrule 166, the washer 154 pushes the catheter ferrule 166 distally with respect to the connector bushing 177. This causes the portion 178 of the inner wall of the catheter ferrule to move away from the connector bushing 177, allowing the connector bushing 177 and the fiber connector 160 to freely rotate within the catheter ferrule 166 without friction or side loading that could compromise performance during operation.

The catheter ferrule 166 is preferably constructed of a rigid, injection moldable material as a one or two piece assembly comprising the cylindrical portion of the ferrule 166 and the shield 164 attached with adhesive. The plastic bag used with IVUS products to serve as a shield can still be used because the non-sterile motor unit is laid in the sterile field, but the bag will not be used as a sterile barrier to protect the clinician's hand from the non-sterile motor unit. Instead, the shield 164 acts as a sterile barrier to prevent the contamination of the clinician's sterile hand during attachment of the catheter to the non-sterile motor unit.

Figure 10:
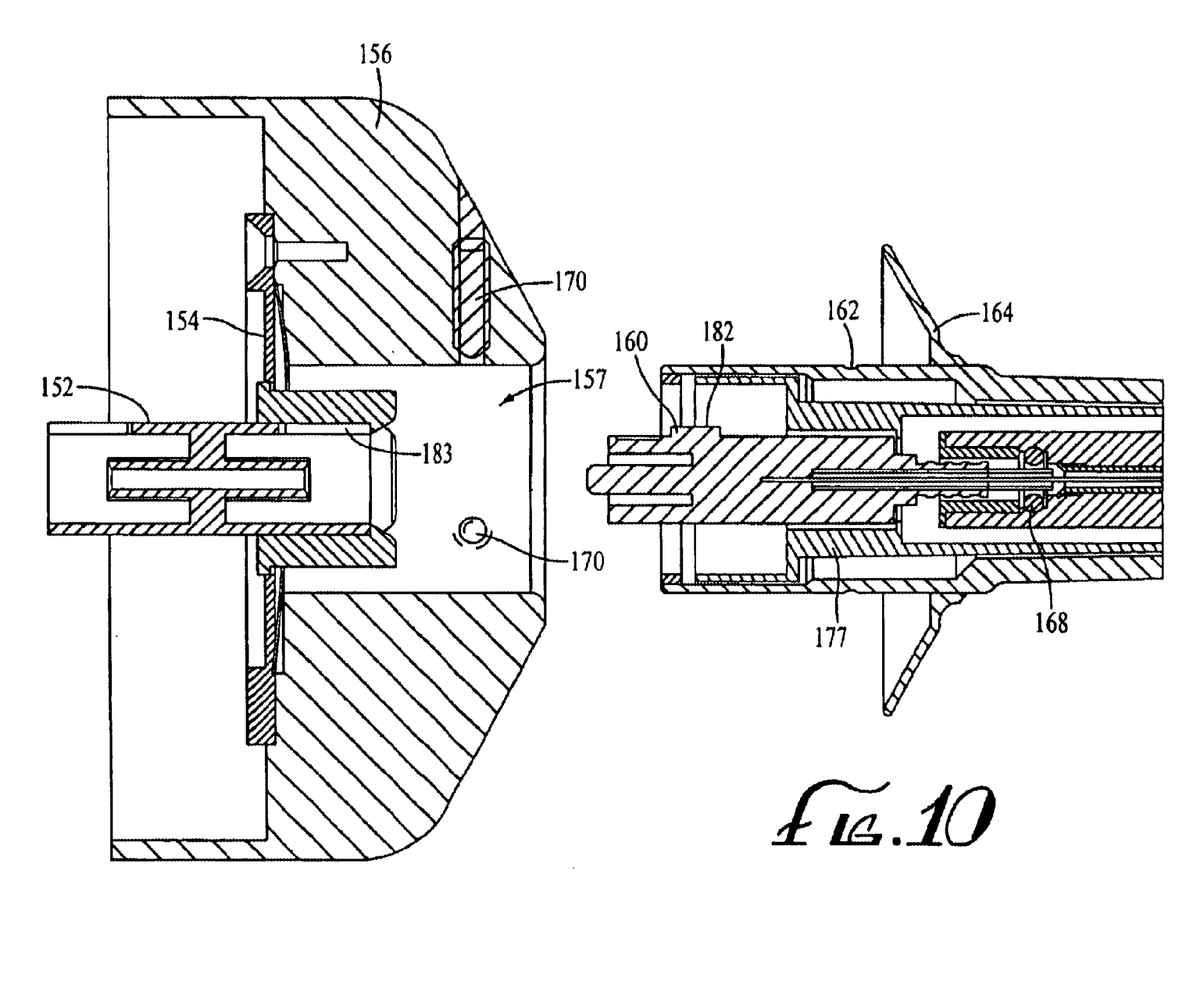
FIG. 10 shows a blown-up cross-sectional view of the OCT connection system in FIG. 9.

Referring to FIGS. 9 and 10, the seal arrangement of this embodiment differs from the previous embodiments. The seal 168, which is preferably an 'O'-ring, seals around a gland 174 instead of a grooved portion of the catheter connector. The gland 174 is a stainless steel tube with a smooth outer surface finish that is bonded into the fiber connector 162 using epoxy to form a high-pressure seal. As in the previous embodiments, an 'O'-ring housing is fitted around the 'O'-ring. Four drain holes 172 are provided on the catheter ferrule to allow fluid leakage to drain through the wall of the ferrule 166 to reduce the likelihood of contamination of the motor unit and the fiber optic connector 162 if the seal should leak during high-pressure infusion.

The catheter connector includes a tab 182 adapted to be received in a slot 183 in the fiber-to-fiber adapter 152. The tab 182 and the slot 183 in the fiber-to-fiber adapter 152 provide for a one-way fit of the catheter connector 150 into the motor unit. This is desirable to prevent an operator from trying to force the catheter fiber connector 160 into the fiber-to-fiber adapter 152 in an improper orientation, which could cause damage to one or both halves of the optical connector mating pair.

While various embodiments of the application have been described, it will be apparent to those of ordinary skill in the art that many more embodiments and implementations are possible that are within the scope of the subject invention. For example, each feature of one embodiment can be mixed and matched with other features shown in other embodiments. Features known to those of ordinary skill in the art of optics may similarly be incorporated as desired. Additionally and obviously, features may be added or subtracted as desired. Therefore, the invention is not to be restricted or limited except in accordance with the following claims and their equivalents.

What is claimed is:

1. An optical catheter connector comprising:
   a flexible hollow catheter ferrule;
   a rigid retainer housed inside the catheter ferrule, wherein the retainer has at least two cutouts;
   a fiber connector housed inside the retainer;
   an optical fiber positioned along a rotational axis of the fiber connector; and
   a connector bushing housed inside the retainer, wherein the connector bushing is attached to the fiber connector and the connector bushing has ribs on its outer surface positioned at, and configured to engage, the cutouts of the retainer for providing proper engagement with a motor unit.

2. The catheter connector of claim 1, wherein the cutouts in the retainer are elliptical.

3. The catheter connector of claim 1, wherein the catheter ferrule is made of a flexible polymer.

4. The catheter connector of claim 1, wherein the retainer is made of polycarbonate.

5. The catheter connector of claim 1, wherein the retainer is made of plastic.

6. The catheter connector of claim 1, further comprising a shield disposed around an outer periphery of the catheter ferrule.

* * * * *